United States Patent [19]

Kawamura et al.

[11] Patent Number: 5,312,798
[45] Date of Patent: May 17, 1994

[54] HERBICIDAL COMPOSITION

[75] Inventors: Shinichi Kawamura, Osaka; Izumi,Keiichi, Hyogo; Junichi Sato, Osaka; Yuzuru Sanemitsu, Hyogo, all of Japan; Ryo Sato, Durham, N.C.; Tatsuhiro Hamada, Hyogo; Hideyuki Shibata, Osaka, both of Japan

[73] Assignee: Sumitomo Chemical Company, Limited, Osaka, Japan

[21] Appl. No.: 944,084

[22] Filed: Sep. 11, 1992

[30] Foreign Application Priority Data

| Sep. 11, 1991 | [JP] | Japan | 3-231847 |
| Sep. 11, 1991 | [JP] | Japan | 3-231848 |
| Sep. 11, 1991 | [JP] | Japan | 3-231849 |
| Sep. 11, 1991 | [JP] | Japan | 3-231850 |
| Sep. 11, 1991 | [JP] | Japan | 3-231851 |

[51] Int. Cl.$^5$ ............... A01N 43/70; A01N 43/58; A01N 43/78; A01N 43/76
[52] U.S. Cl. ............... 504/134; 504/137; 504/138; 504/140; 504/148; 504/216; 504/229; 504/237; 504/243; 504/260; 504/266; 504/271; 504/331; 504/347
[58] Field of Search .............. 504/347, 266, 138, 229, 504/134, 237, 136, 271, 140, 260, 243, 331, 148, 216, 137

[56] References Cited

U.S. PATENT DOCUMENTS

| 3,403,180 | 9/1968 | Soper | 504/347 |
| 4,103,017 | 7/1978 | Davies et al. | 424/270 |
| 4,118,390 | 10/1978 | Wu et al. | 504/266 |
| 4,460,403 | 7/1984 | Takematsu et al. | 504/134 |
| 4,867,780 | 9/1989 | Woolard | 504/252 |
| 4,913,722 | 4/1990 | Felix et al. | 71/90 |
| 4,968,342 | 11/1990 | Forster et al. | 504/263 |

FOREIGN PATENT DOCUMENTS

| 0300906 | 1/1989 | European Pat. Off. |
| 0349282 | 1/1990 | European Pat. Off. |
| 0349283 | 1/1990 | European Pat. Off. |
| 0384244 | 8/1990 | European Pat. Off. |
| 0432600 | 6/1991 | European Pat. Off. |
| 0446802 | 9/1991 | European Pat. Off. |
| 941288 | 6/1956 | Fed. Rep. of Germany |

OTHER PUBLICATIONS

T. Motegi et al, Short Review of Herbicides & PGRs 1991, 6th Edition.

*Primary Examiner*—Allen J. Robinson
*Assistant Examiner*—Deborah Lambkin
*Attorney, Agent, or Firm*—Birch, Stewart, Kolasch & Birch

[57] ABSTRACT

There is disclosed a herbicidal composition comprising as active ingredients a herbicidally effective amount of (a) an iminothiazoline compound of the formula:

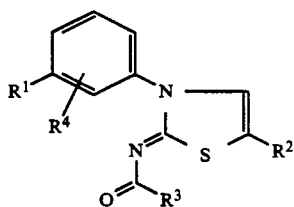

wherein $R^1$ is halogen, halo($C_1$-$C_2$)alkyl, halo($C_1$-$C_2$)alkoxy or halo($C_1$-$C_2$)alkylthio; $R^2$ is $C_1$-$c_2$ alkyl, chroline, bromine or iodine; $R^3$ is $C_1$-$C_6$ alkyl, $C_3$-$C_6$ cycloalkyl, $C_3$-$C_6$ cycloalkoxy or $C_1$-$C_6$ alkoxy, all of which are optionally substituted with at least one substituent selected from halogen, $C_1$-$C_2$ alkyl and $C_1$-$C_2$ alkoxy; $R^4$ is hydrogen or halogen; and (b) at least one of herbicidal triazine compounds, herbicidal uracil compounds, herbicidal urea compounds, herbicidal dinitro aniline compounds, norflurazon, dimethazon, imazaquin and imazethapyr. Also disclosed is a method for controlling undesired weeds by use of the herbicidal composition.

20 Claims, No Drawings

HERBICIDAL COMPOSITION

FIELD OF THE INVENTION

The present invention relates to a herbicidal composition. More particularly, it relates to a herbicidal composition comprising an iminothiazoline compound and at least one of particular herbicidal compounds.

BACKGROUND OF THE INVENTION

A great number of chemical substances having a herbicidal activity have been used for herbicidal agents to exterminate or control the vegetation of undesired weeds in agricultural and non-agricultural fields. However, there are many kinds of weeds and their growth extends over a long period of time, so that most of the conventional herbicidal agents have an effect only on the specific kinds of weeds. Accordingly, there is a great demand on herbicidal agents capable of exerting a strong herbicidal activity against a wide variety of weeds without any material phytotoxicity to crop plants.

By the way, no-till cultivation has recently been developed for saving labor work, extending a cultivation period and preventing loss in weight of soil. For this reason, there also is a great demand on herbicidal agents capable of exerting a distinct herbicidal activity in foliar treatment, maintaining a prolonged herbicidal efficacy in soil treatment and showing a prominent selectivity between crop plants and weeds.

OBJECTS OF THE INVENTION

The present inventors have intensively studied herbicidal agents and found that a highly enhanced herbicidal activity against a wide variety of weeds in agricultural and non-agricultural fields can be attained by the combined use of particular herbicidal compounds.

SUMMARY OF THE INVENTION

The present invention provides a herbicidal composition comprising as active ingredients a herbicidally effective amount of (a) an iminothiazoline compound of the formula:

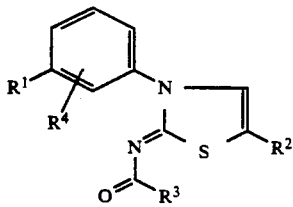

wherein $R^1$ is halogen, halo($C_1$-$C_2$)alkyl, halo($C_1$-$C_2$)alkoxy or halo($C_1$-$C_2$)alkylthio; $R^2$ is $C_1$-$C_2$ alkyl, chroline, bromine or iodine; $R^3$ is $C_1$-$C_6$ alkyl, $C_3$-$C_6$ cycloalkyl, $C_3$-$C_6$ cycloalkoxy or $C_1$-$C_6$ alkoxy, all of which are optionally substituted with at least one substituent selected from halogen, $C_1$-$C_2$ alkyl and $C_1$-$C_2$ alkoxy; $R^4$ is hydrogen or halogen (hereinafter referred to as compound (I)); and (b) at least one of herbicidal triazine compounds, herbicidal uracil compounds, herbicidal urea compounds, herbicidal dinitro aniline compounds, norfrurazon, dimetazon, imazaquin and imazetapia (hereinafter referred to as compound (II)).

DETAILED DESCRIPTION OF THE INVENTION

The herbicidal composition of the present invention is characterized by the combined use of compounds (I) and (II). In comparison with the separate use of each of these compounds, this combined use provides remarkable enhancement of the herbicidal potency, so that they may be used at a smaller dosage. Further, the weed-control spectrum is widely enlarged. Thus, a clear and definite herbicidal effect is observed in the combined use, and the herbicidal composition can be used with high safety for no-till cultivation of crop plants such as cotton, soybean, corn, wheat, barley and rice plant.

The herbicidal composition of the present invention can exterminate or control a variety of weeds, of which examples are broad-leaved weeds such as common puslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), veivetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cooklebur (*Xanthium pensylvanicum*), common sunflower (*Helianthus annuus*), scentless chamomile (*Matricaria perforata*) and corn marigold (*Chrysanthemum segetum*). Examples of Graminaceous weeds include Japanese millet (*Echinochloa frumentacea*), barnyardgrass (*Echinochloa crus-galli*), green foxtail (*Setaria viridis*), yellow foxtail (*Setaria glauca*), southern crabgrass (*Digitaria ciliaris*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), giant foxtail (*Setaria faberi*), fall panicum (*Panicum dichotomiflorum*), shattercane (*Sorghum bicooor*) and bermudagrass (*Cynodon dactylon*). It should be noted that the herbicidal composition of the present invention have the advantage of exhibiting no material chemical injury to various agricultural crops such as corn, wheat, barley, soybean, cotton and rice plant (particularly, to cotton, soybean, corn, wheat and barley when compound (II) is a triazine compound or urea compound; to cotton or soybean when compound (II) is norfrurazon, dimetazon, imazaquin or imazetapia; and to cotton, rice plants or soybean when compound (II) is a dinitro aniline compound).

The compound (I) can be produced according to the process as described in EP-A-0446802. Examples of compound (II) are described by Imamura et al., "Short Review of Herbicides and PGRs 1991", 188–211, 174, 268, 170, 172, 180–183 and 54–91 (1990), such as atrazine, cyanazine, prometryne, metribuzin, simazine, simetryne, ametryne, metamitron (preferably atrazine, cyanazine, prometryne, metribuzin) as triazine compounds; isoprocil, bromacil, lenacil as an uracil compound; fenuron, monuron, monolinuron, buturon, diuron, linuron, metoxuron, chlorotoluron, isoproturon, fluometuron as urea compounds; trifluralin, benefin, pendimethalin, oryzalin, ethalfluralin, prodiamine as dinitro aniline compounds; norflurazon, dimethazone, imazaquin and imazethapyr.

However, the combined use of compounds (I) and (II) has never been attempted.

Among various kinds of compound (I), preferred are those wherein $R^1$ is halo($C_1$–$C_2$)alkyl, more preferably trifluoromethyl; those wherein $R^2$ is $C_1$–$C_2$ alkyl, more preferably methyl; those wherein $R^3$ is $C_1$–$C_6$ alkoxy, $C_1$–$C_6$ alkyl or halo($C_1$–$C_6$)alkyl, more preferably $C_1$–$C_6$ alkyl substituted with fluorine, more preferably methyl substituted with fluorine, more preferably difluoromethyl or trifluoromethyl; and those wherein $R^4$ is hydrogen or fluorine at the para position, more preferably hydrogen. The proportion of compounds (I) and (II) as the active ingredients in the herbicidal composition of the present invention may vary within a considerable broad range. In general, however, herbicidal triazine compounds as compound (II) can be used in an amount of about 0.1 to 100 parts by weight, preferably of about 0.2 to 50 parts by weight, more preferably of about 0.5 to 30 parts by weight; norflurazon, dimetazon, imazaquin or imazethapyr as compound (II) can be used in an amount of about 0.1 to 100 parts by weight, preferably of about 0.2 to 50 parts by weight, more preferably of about 0.3 to 30 parts by weight; herbicidal uracil compounds as compound (II) can be used in an amount of about 0.5 to 100 parts by weight, preferably of about 0.8 to 30 parts by weight, more preferably of about 1 to 20 parts by weight; herbicidal urea compounds as compound (II) can be used in an amount of about 0.1 to 100 parts by weight, preferably of about 0.5 to 50 parts by weight, more preferably of about 0.8 to 30 parts by weight; herbicidal dinitro aniline compounds as compound (II) can be used in an amount of about 0.5 to 100 parts by weight, preferably of about 0.8 to 50 parts by weight, more preferably of about 1 to 30 parts by weight, all to one part by weight of compound (I).

For the practical usage of the herbicidal composition of the present invention, it is usually formulated with conventional solid or liquid carriers or diluents as well as surface active agents, or other auxiliary agents into conventional formulations such as emulsifiable concentrates, wettable powders, suspensions, flowables, granules and water-dispersible granules.

These formulations contain the active ingredients at a total content of from about 0.5% to 90% by weight, preferably from about 1% to 80% by weight.

Examples of the solid carrier or diluent are fine powders or granules of kaolin clay, attapulgite clay, bentonite, terra alba, pyrophyllite, talc, diatomaceos earth, calcite, walnut shell powders, urea, ammonium sulfate and synthetic hydrous silica. As the liquid carrier or diluent, there may be exemplified aromatic hydrocarbons (e.g., xylene, methylnaphthalene), alcohols (e.g., isopropanol, ethylene glycol, ethoxyethanol), ketones (e.g., acetone, cyclohexanone, isophorone), vegetable oil, (e.g., soybean oil, cotton seed oil), dimethylsulfoxide, N,N-dimethylformamide, acetonitrile and water.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymers, sorbitan fatty acid esters and polyoxyethylene sorbitan fatty acid esters. Examples of the auxiliary agent include ligninsulfonates, sodium alginate, polyvinyl alcohol, gum arabic, CMC (carboxymethyl cellulose) and PAP (isopropyl acid phosphate).

The herbicidal composition thus formulated in any suitable formulation is useful for pre-emergence or post-emergence control of undesired weeds by soil or foliar treatment. These treatments include application to the soil surface prior to or after planting, incorporation into the soil prior to planting or transplanting, and the like. The foliar treatment may be effected by spraying the herbicidal composition over the top of plants. It may also be applied directly to the weeds if care must be taken to keep the chemical off the crop foliage.

The dosage of the active ingredients may vary depending on the active ingredient species, mixing ratio, formulation used, prevailing weather conditions, prevailing season, mode of application, soil involved, crop and weed species, and the like. Usually, however, the total dosage of the active ingredients is (a) from about 100 to 4000 grams, preferably from 150 to 3000 grams, more preferably from 200 to 2000 grams per hectare, when herbicidal triazine compounds, urea compounds and dinitro aniline compounds are used; (b) from 100 to 20,000 grams, preferably from 150–5000 grams, more preferably 200–2000 grams per hectare, when herbicidal uracil compounds are used; and (c) from 50 to 3000 grams, preferably 100 to 2500 grams, more preferably 150 to 2000 grams per hectare, when norfluazon, dimethazone, imazaquin and imazethapyr are used. The herbicidal composition formulated in the form of an emulsifiable concentrate, wettable powder, suspensions, flowable or water-dispersible granules may usually be employed by diluting it with water at a volume of about 100 to 1000 liters per hectare, if necessary, with addition of an auxiliary agent such as a spreading agent. The herbicidal composition formulated in the form of granules may usually be applied as such without dilution.

Examples of the spreading agent include, in addition to the surface active agents as noted above, polyoxyethylene resin acid (ester), ligninsulfonate, abietylenic acid salts, dinaphthylmethandisulfonate and paraffin.

The herbicidal composition of the present invention is useful as a herbicide to be employed for paddy field, crop field, orchards, pasture land, lawns, forests and non-agricultural fields. Furthermore, it may be applied in combination with insecticides, acaricides, nematocides, fungicides, other herbicides, plant growth regulators, fertilizers, soil improvers and the like.

The present invention will be explained in more detail by way of Reference Examples, Formulation Examples and Test Examples, to which however the invention is not limited in any way.

Practical embodiments for production of compound (I) are illustrated in the following examples.

REFERENCE PREPARATION EXAMPLE 1

To 2-imino-3-[(3-trifluoromethyl)phenyl]-5-methylthiazoline hydrochloride (7.2 g) in ethyl acetate (100 ml), added were triethylamine (7.4 g) and trifluoroacetic acid anhydride (5.2 g) with stirring at room temperature, and stirring was continued for 3 hours. The residue was washed with water (50 ml) and dried over anhydrous magnesium sulfate. The solvent was removed under reduced pressure to give a crystalline residue which was recrystallized from isopropanol to afford 2-[(trifluoroacetyl)imino]-3-[(3-trifluoromethyl)- phenyl]-5-methylthiazoline (Compound No. 46) (7.5 g). m.p., 128.1° C.

REFERENCE PREPARATION EXAMPLE 2

A mixture of 2-imino-3-[(3-trifluoromethyl)phenyl]-5-methylthiazoline hydrochloride (0.42 g), triethylamine (2.2 g), 1-ethyl-3-(3-dimethylaminopropyl)carbodiimide hydrochloride (0.8 g) and difluoroacetic acid (0.75 g) in chloroform (10 ml) was refluxed for 8 hours. After cooling, the residue was washed with aqueous hydrochloric acid and aqueous potassium carbonate, and dried over anhydrous magnesium sulfate. The solvent was removed under reduced pressure, and the residue was subjected to column chromatography to give 2-[(difluoroacetyl)imino]-3-[(3-trifluoromethyl)phenyl]-5-methylthiazoline (Compound No. 55) (0.3 g). m.p., 117.9° C.

REFERENCE PREPARATION EXAMPLE 3

A solution of 2-[(ethoxycarbonyl)imino]-3-[(3-trifluoromethyl)phenyl]thiazoline (0.5 g) and N-iodosuccinimide (0.4 g) in chloroform (30 ml) was refluxed for 20 hours. After cooling, the reaction mixture was washed with an aqueous sodium sulfite solution and dried over anhydrous magnesium sulfate. The solvent was removed under reduced pressure, and the residue was subjected to column chromatography to give 0.1 g of 2-[(ethoxycarbonyl)imino]-3-[(3-trifluoromethyl)-phenyl]-5-iodothiazoline (Compound No. 38).

In the same manner as above, various kinds of compounds (I) as shown in Table 1 were obtained.

TABLE 1

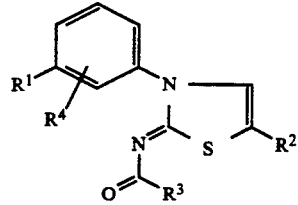

| Compound No. | $R^1$ | $R^2$ | $R^3$ | $R^4$ | m.p. (°C.) |
|---|---|---|---|---|---|
| 1 | $CF_3$ | $CH_3$ | $OC_2H_5$ | H | 115.5 |
| 2 | $CF_3$ | $C_2H_5$ | $OC_2H_5$ | H | 97.1 |
| 3 | $CF_3$ | $CH_3$ | $OCH_3$ | H | 136.8 |
| 4 | $CF_3$ | $CH_3$ | $O\text{-}i\text{-}C_3H_7$ | H | 126.0 |
| 5 | $CF_3$ | $C_2H_5$ | $O\text{-}i\text{-}C_3H_7$ | H | 91.8 |
| 6 | $CF_3$ | $CH_3$ | $O\text{-}n\text{-}C_3H_7$ | H | 91.1 |
| 7 | $CF_3$ | $CH_3$ | O-cyclopentyl | H | 134.0 |
| 8 | $CF_3$ | $CH_3$ | O-cyclohexyl | H | 155.7 |
| 9 | $CF_3$ | $CH_3$ | $OCH_2CH_2OCH_3$ | H | 103.0 |
| 10 | $CF_3$ | $CH_3$ | $OCH_2CH(CH_3)_2$ | H | 101.6 |
| 11 | $CF_3$ | $CH_3$ | $OCH(CH_3)C_2H_5$ | H | 107.8 |
| 12 | $CF_3$ | $C_2H_5$ | $OCH_3$ | H | 141.4 |
| 13 | $CF_3$ | $C_2H_5$ | $CH_2CH(CH_3)_2$ | H | 116.3 |
| 14 | $CF_3$ | $CH_3$ | cyclopropyl | H | 132.6 |
| 15 | $CF_3$ | $CH_3$ | $CH_2C(CH_3)_3$ | H | 123.1 |
| 16 | $OCF_3$ | $CH_3$ | $OC_2H_5$ | H | 102.1 |
| 17 | $OCF_3$ | $CH_3$ | $O\text{-}i\text{-}C_3H_7$ | H | 120.0 |
| 18 | $CF_3$ | $C_2H_5$ | cyclopropyl | H | 111.7 |
| 19 | $CF_3$ | $C_2H_5$ | $O\text{-}n\text{-}C_3H_7$ | H | 75.7 |
| 20 | $CF_3$ | $CH_3$ | $i\text{-}C_3H_7$ | H | 139.6 |
| 21 | $CF_3$ | $CH_3$ | $n\text{-}C_4H_9$ | H | 122.6 |
| 22 | $OCF_3$ | $C_2H_5$ | $O\text{-}i\text{-}C_3H_7$ | H | 63.6 |
| 23 | $CF_3$ | $CH_3$ | cyclopropyl-$CH_3$ | H | 100.3 |
| 24 | $CF_3$ | $CH_3$ | $C(CH_3)_3$ | H | 94.7 |
| 25 | $CF_3$ | $CH_3$ | $CH_2CH(CH_3)_2$ | H | 92.4 |
| 26 | $CF_3$ | $CH_3$ | $CH(CH_3)CH_2CH_3$ | H | 58.3 |
| 27 | $CF_3$ | Br | $OC_2H_5$ | H | 136.8 |
| 28 | $CF_3$ | Cl | $OC_2H_5$ | H | 138.2 |
| 29 | $CF_3$ | Br | $O\text{-}i\text{-}C_3H_7$ | H | 106.0 |
| 30 | $CF_3$ | Br | $OCH_3$ | H | 106.8 |
| 31 | $CF_3$ | Br | $n\text{-}C_3H_7$ | H | 141.4 |
| 32 | $CF_3$ | Br | $O\text{-}n\text{-}C_4H_9$ | H | 104.9 |
| 33 | F | Br | $OC_2H_5$ | H | 172.4 |
| 34 | Br | Br | $OC_2H_5$ | H | 155.4 |
| 35 | Cl | Br | $OC_2H_5$ | H | 147.7 |
| 36 | $CF_3$ | Br | $OC_6H_5$ | H | 137.7 |
| 37 | $CF_3$ | Br | $O\text{-}n\text{-}C_3H_7$ | H | 107.0 |
| 38 | $CF_3$ | I | $OC_2H_5$ | H | 121.6 |
| 39 | $CF_3$ | $CH_3$ | $CH_2CH_2Cl$ | H | 155.2 |
| 40 | $CF_3$ | $CH_3$ | $C_2H_5$ | H | 164.6 |
| 41 | $CF_3$ | $CH_3$ | $C_3H_7$ | H | 111.0 |
| 42 | $CF_3$ | $C_2H_5$ | $CH_3$ | H | 87.8 |
| 43 | $CF_3$ | $C_2H_5$ | $C_2H_5$ | H | 117.5 |
| 44 | $CF_3$ | $C_2H_5$ | $n\text{-}C_3H_7$ | H | 119.0 |
| 45 | $CF_3$ | $C_2H_5$ | $i\text{-}C_3H_7$ | H | 96.6 |
| 46 | $CF_3$ | $CH_3$ | $CF_3$ | H | 128.1 |
| 47 | $CF_3$ | $C_2H_5$ | $CF_3$ | H | 92.0 |
| 48 | $CF_3$ | Br | $CF_3$ | H | 113.2 |
| 49 | $CF_3$ | $CH_3$ | $C_2F_5$ | H | 98.5 |
| 50 | $CF_3$ | $C_2H_5$ | $C_2F_5$ | H | 94.1 |
| 51 | $CF_3$ | $CH_3$ | $C_3F_7$ | H | 61.7 |
| 52 | $OCF_3$ | $CH_3$ | $CH_3$ | H | 150.8 |
| 53 | $OCF_3$ | $CH_3$ | $CF_3$ | H | 104.7 |
| 54 | $CF_3$ | $C_2H_5$ | cyclopropyl-$CH_3$ | H | 98.3 |
| 55 | $CF_3$ | $CH_3$ | $CHF_2$ | H | 117.9 |
| 56 | $CF_3$ | $CH_3$ | $CH_2F$ | H | 135.7 |
| 57 | $CF_3$ | $C_2H_5$ | $CHF_2$ | H | 96.3 |
| 58 | $CF_3$ | $CH_3$ | $CH_3$ | 4-F | 179.0 |
| 59 | $CF_3$ | $CH_3$ | $CF_3$ | 4-F | 119.4 |
| 60 | $CF_3$ | $CH_3$ | $i\text{-}C_3H_7$ | 4-F | 133.2 |
| 61 | $CF_3$ | $CH_3$ | $O\text{-}i\text{-}C_3H_7$ | 4-F | 130.8 |
| 62 | $CF_3$ | $CH_3$ | $CF_3$ | 6-F | 144.7 |
| 63 | $CF_3$ | $CH_3$ | $O\text{-}i\text{-}C_3H_7$ | 6-F | 158.5 |
| 64 | $CF_3$ | $CH_3$ | $CH_3$ | 4-Cl | 187.9 |
| 65 | $CF_3$ | $CH_3$ | $CF_3$ | 4-Cl | 134.2 |
| 66 | $CF_3$ | $CH_3$ | cyclopropyl | 4-Cl | 166.2 |
| 67 | $CF_3$ | $CH_3$ | $CHF_2$ | 4-F | 139.9 |
| 68 | $CF_3$ | $C_2H_5$ | $CH_3$ | 4-F | 131.4 |
| 69 | $CF_3$ | $C_2H_5$ | $CF_3$ | 4-F | 84.6 |

TABLE 1-continued

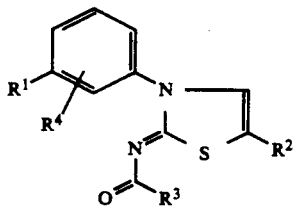

| Compound No. | R¹ | R² | R³ | R⁴ | m.p. (°C.) |
|---|---|---|---|---|---|
| 70 | CF₃ | C₂H₅ | CHF₂ | 4-F | 117.0 |

Practical embodiments for preparation of the composition are illustrated in the following Formulation Examples wherein parts are by weight.

FORMULATION EXAMPLE 1

Eight parts of compound (I), 40 parts of prometryn, atrazine, dimetazon, imazetapia, diuron, fenuron, linuron, chlorotoluron, trifluralin, benefin or prodiamine, 3 parts of calcium ligninsulfonate, 2 parts of sodium laurylsulfate and 47 parts of synthetic hydrated silica are well mixed while being powdered to obtain a wettable powder.

FORMULATION EXAMPLE 2

Twelve parts of compound (I), 12 parts of metribuzin or bromacil, 3 parts of polyoxyethylene sorbitan monooleate, 3 parts of CMC and 70 parts of water are mixed and pulverized until the particle size becomes less than 5 microns to obtain a suspension.

FORMULATION EXAMPLE 3

Three tenths parts of compound (I), 9 parts of cyanazine, norflurazon, isoproturon, trifluralin or pendimethalin, 2 parts of calcium ligninsulfonate, 1 part of synthetic hydrated silica and 30 parts of bentonite and 57.7 parts of kaolin clay are well mixed while being powdered. The mixture is then kneaded with water, granulated and dried to obtain granules.

FORMULATION EXAMPLE 4

Thirty four parts of compound (I), 17 parts of metribuzin, 3 parts of calcium ligninsulfonate, 2 parts of sodium laurylsulfate and 44 parts of synthetic hydrated silica are well mixed while being powdered to obtain a wettable powder.

FORMULATION EXAMPLE 5

One and a half parts of compound (I), 45 parts of prometryn or bromacil, 3 parts of calcium ligninsulfonate, 2 parts of sodium laurylsulfate and 48.5 parts of synthetic hydrated silica are well mixed while being powdered to obtain a wettable powder.

FORMULATION EXAMPLE 6

Twenty parts of compound (I), 6 parts of imazaquin, 3 parts of polyoxyethlene sorbitan monooleate, 3 parts of CMC and 68 parts of water are mixed and pulverized until the particle size becomes less than 5 microns to obtain a suspension.

FORMULATION EXAMPLE 7

Fourty parts of compound (I), 8 parts of imazatapyr, 3 parts of calcium ligninsulfonate, 2 parts of sodium laurylsulfate and 47 parts of synthetic hydrated silica are well mixed while being powdered to obtain a wettable powder.

FORMULATION EXAMPLE 8

Six parts of compound (I), 30 parts of norflurazon, 2 parts of calcium ligninsulfonate, 1 part of synthetic hydrated silica and 30 parts of bentonite and 31 parts of kaolin clay are well mixed while being powdered. The mixture is then kneaded with water, granulated and dried to obtain granules.

FORMULATION EXAMPLE 9

One part of compound (I), 50 parts of norfrurazon, fluometuron or trifluralin, 3 parts of calcium ligninsulfonate, 2 parts of sodium laurylsulfate and 44 parts of synthetic hydrated silica are well mixed while being powdered to obtain a wettable powder.

FORMULATION EXAMPLE 10

Seven parts of compound (I), 42 parts of bromacil, 3 parts of calcium ligninsulfonate, 2 parts of sodium laurylsulfate and 46 parts of synthetic hydrated silica are well mixed while being powdered to obtain a wettable powder.

FORMULATION EXAMPLE 11

A half part of compound (I), 10 parts of bromacil, 2 parts of calcium ligninsulfonate, 1 part of synthetic hydrated silica and 30 parts of bentonite and 56.5 parts of kaolin clay are mixed well while being powdered. The mixture is then kneaded with water, granulated and dried to obtain granules.

FORMULATION EXAMPLE 12

Twenty five parts of compound (I), 20 parts of lenacil, trifluralin, 3 parts of calcium ligninsulfonate, 2 parts of sodium laurysulfate and 50 parts of synthetic hydrated silica are well mixed while being powdered to obtain a wettable powder.

FORMULATION EXAMPLE 13

One part of compound (I), 30 parts of isoprocil, 3 parts of calcium ligninsulfonate, 2 parts of sodium laurylsulfate and 64 parts of synthetic hydrated silica are well mixed while being powdered to obtain a wettable powder.

FORMULATION EXAMPLE 14

Fifteen parts of compound (I), 12 parts of fluometuron, 3 parts of polyoxyetylene sorbitan monooleate, 3 parts of CMC and 67 parts of water are mixed and pulverized until the particle size becomes less than 5 microns to obtain a suspension.

FORMULATION EXAMPLE 15

Thirty parts of compound (I), 15 parts of diuron, 3 parts of calcium ligninsulfonate, 2 parts of sodium laurylsulfate and 50 parts of synthetic hydrated silica are well mixed while being powdered to obtain a wettable powder.

FORMULATION EXAMPLE 16

Eight parts of compound (I), 20 parts of trifluralin, oryzalin or ethalfluralin, 3 parts of polyoxyethylene sorbitan monooleate, 3 parts of CMC and 66 parts of water are mixed and pulverized until the particle size becomes less than 5 microns to obtain a suspension.

FORMULATION EXAMPLE 17

Fourteen parts of compound (I), 14 parts of trifluralin, 3 parts of calcium ligninsulfonate, 2 parts of sodium laurylsulfate and 47 parts of synthetic hydrated silica are well mixed while being powdered to obtain a wettable powder.

The practical herbicidal activity of the composition of the invention will be explained in further detail with reference to the following Test Examples wherein the growth controlling percentage (%) was determined by weighing the aerial parts of the test plants (fresh weight) and making calculation according to the following equation:

$$\text{Growth controlling percentage (\%)} = \left\{ 1 - \frac{\text{Fresh weight of test plant in treated plot}}{\text{Fresh weight of test plant in untreated plot}} \right\} \times 100$$

TEST EXAMPLE 1

Vats (33 cm × 23 cm × 11 cm) were filled with upland field soil, and the seeds of the test plants (except for cotton) were sowed therein in 1 to 2 cm depth. A designated amount of the test composition formulated in an wettable powder as in Formulation Example 1 was diluted with a water, and the dilution was sprayed onto the soil surface by means of an automatic sprayer at a spray volume of 1000 liters per hectare. Thereafter, the soil surface (to 4 cm depth) was well mixed and the seeds of cotton were sowed in 2 cm depth. The test plants were grown in a green house for 28 days, and the herbicidal activity and phytotoxicity were examined. The results are shown in Table 2.

TABLE 2

| Test compound | Active ingredient dosage (g/ha) | Mixing ratio | Phytotoxicity Cotton | Herbicidal activity | | | | |
|---|---|---|---|---|---|---|---|---|
| | | | | Bermuda-grass | Fall panicum | Goose-grass | Hemp sesbania | Common cocklebur |
| Promet-ryn | 500 | — | none | 75 | 25 | 0 | 85 | 5 |
| | 1000 | — | none | 97 | 80 | 50 | 90 | 94 |
| | 2000 | — | none | 100 | 95 | 80 | 95 | 98 |
| Compound No. 4 + Promet-ryn | 100 + 500 | 1:5 | none | 100 | 100 | 100 | 100 | 71 |
| | 100 + 1000 | 1:10 | none | 100 | 100 | 100 | 100 | 100 |
| | 200 + 500 | 1:2.5 | none | 100 | 100 | 100 | 100 | 98 |
| | 200 + 1000 | 1:5 | none | 100 | 100 | 100 | 100 | 100 |
| Compound No. 55 + Promet-ryn | 100 + 1000 | 1:10 | none | 100 | 100 | 100 | 100 | 100 |
| | 200 + 1000 | 1:5 | none | 100 | 100 | 100 | 100 | 100 |

TEST EXAMPLE 2

Concrete containers (40 cm × 35 cm) were filled with upland field soil, and the seeds of the test plants were sowed therein in 1 to 3 cm depth. A designated amount of the test composition formulated in an wettable powder as in Formulation Example 1 was diluted with water, and the dilution was sprayed onto the soil surface by means of a small hand sprayer at a spray volume of 430 liters per hectare. The test plants treated with the test compositions as described above were grown outdoors for 52 days, and the herbicidal activity and phytotoxicity were examined. The results are shown in Table 3.

TABLE 3

| Test compound | Active ingredient dosage (g/ha) | Mixing ratio | Phytotoxicity Soybean | Herbicidal activity | | | |
|---|---|---|---|---|---|---|---|
| | | | | Southern crabgrass | Giant foxtail | Slender amaranth | Jimson-weed |
| Metri-buzin | 200 | — | none | 10 | 10 | 65 | 30 |
| | 400 | — | none | 50 | 25 | 95 | 30 |
| Compound No. 4 + Metri-buzin | 200 + 200 | 1:1 | none | 100 | 100 | 95 | 85 |
| | 200 + 400 | 1:2 | none | 100 | 100 | 100 | 100 |

TEST EXAMPLE 3

The test plants in Table 4, which had been treated with the test compositions in Table 4 in the same manner as in Test Example 2, were grown outdoors for 29 days, and herbicidal activity and phytotoxicity were examined. The results are shown in Table 4.

TABLE 4

| Test compound | Active ingredient dosage (g/ha) | Mixing ratio | Phytotoxicity Corn | Herbicidal activity | | | | | |
|---|---|---|---|---|---|---|---|---|---|
| | | | | Johnson-grass | Giant foxtail | Morning-glories | Velvet-leaf | Slender amaranth | Black night-shade |
| Cyana-zine | 600 | — | none | 0 | 0 | 0 | 0 | 0 | 85 |
| | 1200 | — | none | 65 | 80 | 98 | 75 | 0 | 100 |
| Com-pound No. 46 + | 40 + 600 | 1:15 | none | 70 | 100 | 100 | 100 | 100 | 100 |
| | 80 + 600 | 1:7.5 | none | 93 | 100 | 100 | 100 | 100 | 100 |

TABLE 4-continued

| Test compound | Active ingredient dosage (g/ha) | Mixing ratio | Phytotoxicity Corn | Herbicidal activity | | | | | |
|---|---|---|---|---|---|---|---|---|---|
| | | | | Johnsongrass | Giant foxtail | Morningglories | Velvetleaf | Slender amaranth | Black nightshade |
| Cyanazine | | | | | | | | | |

TEST EXAMPLE 4

Sandy plowed fields were turned up and, after border builiding, plotted into blocks of 3 m² (1×3 m²) each. Seeds of the test plants in Table 5 were sowed therein in 4 to 5 cm depth. A designated amount of the test composition formulated in an wettable powder as in Formulation Example 1 was diluted with water, and the dilution was sprayed onto the soil surface by means of a small hand sprayer at a spray volume of 236 liters per hectare. Thereafter, the test plants were grown outdoors for 51 days, and the herbicidal activity and phytotoxicity were examined. The results are shown in Table 5.

TABLE 5

| Test compound | Active ingredient dosage (g/ha) | Mixing ratio | Phytotoxicity Corn | Herbicidal activity | | |
|---|---|---|---|---|---|---|
| | | | | Johnsongrass | Giant foxtail | Slender amaranth |
| Cyanazine | 500 | — | none | 20 | 13 | 13 |
| | 1000 | — | none | 60 | 27 | 15 |
| | 2000 | — | none | 67 | 73 | 40 |
| Compound No. 4 + Cyanazine | 200 + 500 | 1:2.5 | none | 100 | 100 | 100 |
| | 200 + 1000 | 1:5 | none | 100 | 100 | 100 |

TEST EXAMPLE 5

Sandy plowed fields were turned up and, after border builiding, plotted into blocks of 3 m² (1×3 m²) each. Seeds of the test plants in Table 6 were sowed therein in 1 to 7 cm depth. A designated amount of the test composition formulated in an wettable powder as in Formulation Example 1 was diluted with water, and the dilution was sprayed onto the soil surface by means of a small hand sprayer at a spray volume of 236 liters per hectare. Thereafter, the test plants were grown outdoors for 44 days, and the herbicidal activity and phytotoxicity were examined. The results are shown in Table 6.

TABLE 6

| Test compound | Active ingredient dosage (g/ha) | Mixing ratio | Phytotoxicity Soybean | Herbicidal activity | | |
|---|---|---|---|---|---|---|
| | | | | Velvetleaf | Slender amaranth | Pale smartweed |
| Metribuzin | 250 | — | none | 87 | 7 | 77 |
| | 500 | — | none | 100 | 30 | 92 |
| Compound No. 4 + Metribuzin | 100 + 250 | 1:2.5 | none | 100 | 95 | 100 |
| | 200 + 250 | 1:1.25 | none | 100 | 95 | 100 |

TEST EXAMPLE 6

Sandy plowed fields were turned up and, after border builiding, plotted into blocks of 3 m² (1×3 m²) each. Seeds of the test plants in Table 6 (except for cotton) were sowed therein in 1 to 7 cm depth. A designated amount of the test composition formulated in a wettable powder as in Formulation Example 1 was diluted with water, and the dilution was sprayed onto the soil surface by means of a small hand sprayer at a spray volume of 236 liters per hectare. Thereafter, the soil surface (to 7-8 cm depth) was well mixed and the seeds of cotton were sowed therein in 5 to 7 cm depth, the test plants were grown outdoors for 27 days, and the herbicidal activity and phytotoxicity were examined. The results are shown in Table 7.

TABLE 7

| Test compound | Active ingredient dosage (g/ha) | Mixing ratio | Phytotoxicity Cotton | Herbicidal activity | | | |
|---|---|---|---|---|---|---|---|
| | | | | Goosegrass | Southern crabgrass | Prickly side | Common purslane |
| Prometryn | 500 | — | none | 0 | 0 | 20 | 0 |
| | 1000 | — | none | 0 | 13 | 20 | 30 |
| Compound No. 46 + Promet | 100 + 500 | 1:5 | none | 83 | 100 | 100 | 100 |

TABLE 7-continued

| Test compound | Active ingredient dosage (g/ha) | Mixing ratio | Phytotoxicity Cotton | Herbicidal activity | | | |
|---|---|---|---|---|---|---|---|
| | | | | Goosegrass | Southern crabgrass | Prickly side | Common purslane |
| ryn | | | | | | | |

TEST EXAMPLE 7

Sandy plowed fields were turned up and, after border builiding, plotted into blocks of 3 m² (1×3 m²) each. Seeds of the test plants in Table 8 (except for cotton) were sowed therein in 1 to 7 cm depth. A designated amount of the test composition formulated in an wettable powder as in Formulation Example 1 was diluted with water containing a spreading agent, and the dilution was sprayed onto the soil surface by means of a small hand sprayer at a spray volume of 236 liters per hectare. Thereafter, the soil surface (to 7-8 cm depth) was well mixed and the seeds of cotton were sowed therein in 5 to 7 cm depth, the test plants were grown outdoors for 27 days, and the herbicidal activity and phytotoxicity were examined. The results are shown in Table 8.

TABLE 8

| Test compound | Active ingredient dosage (g/ha) | Mixing ratio | Phytotoxicity Cotton | Herbicidal activity | | | |
|---|---|---|---|---|---|---|---|
| | | | | Slender amaranth | Prickly side | Common purslane | Sicklepod |
| Norflurazon | 750 | — | none | 17 | 58 | 33 | 13 |
| | 1500 | — | none | 23 | 92 | 90 | 67 |
| Compound No. 4 + Norfrurazon | 200 + 750 | 1:3.75 | none | 100 | 100 | 100 | 100 |
| Compound No. 46 + Norfrurazon | 100 + 750 | 1:7.5 | none | 100 | 100 | 100 | 100 |
| Compound No. 55 + Norfrurazon | 100 + 750 | 1:7.5 | none | 100 | 100 | 100 | 100 |

TEST EXAMPLE 8

The test plants in Table 9 were treated with the test compositions in Table 9 and grown in the same manner as in Test Example 2. The herbicidal activity and phytotoxicity were examined. The results are shown in Table 9.

TABLE 9

| Test compound | Active ingredient dosage (g/ha) | Mixing ratio | Phytotoxicity Soybean | Herbicidal activity | | | |
|---|---|---|---|---|---|---|---|
| | | | | Quackgrass | Johnsongrass | Southern crabgrass | Slender amaranth |
| Dimethazone | 400 | — | none | 10 | 60 | 50 | 40 |
| | 800 | — | none | 80 | 90 | 50 | 75 |
| Compound No. 4 + Dimetazone | 200 + 400 | 1:2 | none | 100 | 100 | 100 | 100 |

TEST EXAMPLE 9

Sandy plowed fields were turned up and, after border builiding, plotted into blocks of 3 m² (1×3 cm²) each. Seeds of the test plants in Table 10 were sowed therein in 4 to 8 cm depth. A designated amount of the test composition formulated in an wettable powder as in Formulation Example 1 was diluted with water, and the dilution was sprayed onto the soil surface by means of a small hand sprayer at a spray volume of 236 liters per hectare. Thereafter, the test plants were grown outdoors for 44 days, and the herbicidal activity and phytotoxicity were examined. The results are shown in Table 10.

TABLE 10

| Test compound | Active ingredient dosage (g/ha) | Mixing ratio | Phytotoxicity Soybean | Herbicidal activity | | | |
|---|---|---|---|---|---|---|---|
| | | | | Giant foxtail | Southern crabgrass | Morningglories | Jimsonweed |
| Imazaquin | 70 | — | none | 50 | 7 | 50 | 40 |

TABLE 10-continued

| Test compound | Active ingredient dosage (g/ha) | Mixing ratio | Phytotoxicity Soybean | Herbicidal activity | | | |
|---|---|---|---|---|---|---|---|
| | | | | Giant foxtail | Southern crabgrass | Morningglories | Jimsonweed |
| | 140 | — | none | 68 | 43 | 67 | 67 |
| | 280 | — | none | 85 | 52 | 82 | 82 |
| Compound No. 4 + Imazaquin | 100 + 70 | 1:0.7 | none | 100 | 100 | 100 | 100 |
| | 100 + 140 | 1:1.4 | none | 100 | 100 | 100 | 100 |

TEST EXAMPLE 10

Sandy plowed fields were turned up and, after border builiding, plotted into blocks of 3 m² (1×3 m²) each. Seeds of the test plants in Table 11 were sowed therein and cultivated outdoors for 41 days. A designated amount of the test composition formulated in a wettable powder as in Formulation Example 1 was diluted with water containing a spreading agent, and the dilution was sprayed over the foliage of the test plants by means of a small hand sprayer at a spray volume of 236 liters per hectare. At the time of the treatment, the test plants had 9-24 cm in height and 3.5-8 leaves. Thereafter, the test plants were grown outdoors for 43 days, and the herbicidal activity and phytotoxicity were examined. The results are shown in Table 11.

TABLE 11

| Test compound | Active ingredient dosage (g/ha) | Mixing ratio | Herbicidal activity | | | | | | |
|---|---|---|---|---|---|---|---|---|---|
| | | | Persian speedwell | Common purslane | Lambsquarters | Curly dock | Common chickweed | Slender amaranth | Asiatic dayflower |
| Bromacil | 1200 | — | 53 | 88 | 70 | 75 | 10 | 43 | 80 |
| | 2400 | — | 88 | 100 | 90 | 98 | 10 | 53 | 100 |
| Compound No. 46 + Bromacil | 100 + 1200 | 1:12 | 100 | 100 | 100 | 100 | 70 | 97 | 100 |
| | 200 + 1200 | 1:6 | 100 | 100 | 100 | 100 | 100 | 100 | 100 |

TEST EXAMPLE 11

Concrete containers (40 cm×35 cm) were filled with upland field soil, and the seeds of the test plants in Table 12 were sowed therein in 1 to 3 cm depth. A designated amount of the test composition formulated in an wettable powder as in Formulation Example 1 was diluted with water, and the dilution was sprayed onto the soil surface by means of a small hand sprayer at a spray volume of 658 liters per hectare. The test plants treated with the test compositions as described above were grown outdoors for 30 days, and the herbicidal activity and phytotoxicity were examined. The results are shown in Table 12.

TABLE 12

| Test compound | Active ingredient dosage (g/ha) | Mixing ratio | Phytotoxicity Cotton | Herbicidal activity | | | | |
|---|---|---|---|---|---|---|---|---|
| | | | | Prickly side | Velvetleaf | Goosegrass | Southern crabgrass | Bermudagrass |
| Fluometuron | 500 | — | none | 0 | 0 | 0 | 60 | 35 |
| | 1000 | — | none | 30 | 0 | 55 | 70 | 50 |
| Compound No. 46 + Fluometuron | 50 + 500 | 1:10 | none | 70 | 100 | 100 | 100 | 100 |
| | 100 + 500 | 1:5 | none | 100 | 100 | 100 | 100 | 100 |
| Compound No. 55 + Fluometuron | 100 + 500 | 1:5 | none | 100 | 100 | 100 | 100 | 100 |

TEST EXAMPLE 12

Concrete containers (40 cm×35 cm) were filled with upland field soil, and the seeds of the test plants in Table 13 were sowed therein, and cultivated outdoors for 29 days. A designated amount of the test composition formulated in an wettable powder as in Formulation Example 1 was diluted with water containing a spreading agent, and the dilution was sprayed over the foliage of the test plants by means of a small hand sprayer at a spray volume of 658 liters per hectare. At the time of the treatment, the test plants had 1-3 cm in height and 1-2 leaves. Thereafter, the test plants were grown outdoors for 39 days, and the herbicidal activity and phytotoxicity were examined. The results are shown in Table 13.

TABLE 13

| Test compound | Active ingredient dosage (g/ha) | Mixing ratio | Herbicidal activity | | | | | |
|---|---|---|---|---|---|---|---|---|
| | | | Ladys-thumb | Common chick-weed | Field pansy | Purple dead-nettle | Catch-weed bedstraw | Persian speed-well |
| Isoproturon | 500 | — | 60 | 50 | 10 | 0 | 0 | 0 |
| | 1000 | — | 100 | 100 | 25 | 15 | 0 | 0 |
| Compound No. 4 + Isoproturon | 63 + 500 | 1:8 | 100 | 100 | 90 | 80 | 80 | 100 |
| Compound No. 46 + Isoproturon | 63 + 500 | 1:8 | 100 | 100 | 100 | 100 | 90 | 100 |

TEST EXAMPLE 13

The test plants in Table 14 were treated with the test compositions in Table 14 and grown in the same manner as in Test Example 10. The herbicidal activity and phytotoxicity were examined. The results are shown in Table 14.

TABLE 14

| Test compound | Active ingredient dosage (g/ha) | Mixing ratio | Herbicidal activity | | | | |
|---|---|---|---|---|---|---|---|
| | | | Persian speed-well | Lambs-quarters | Slender amaranth | Ladys-thumb | Common chick-weed |
| Diuron | 1200 | — | 23 | 85 | 83 | 40 | 10 |
| | 2400 | — | 48 | 87 | 97 | 78 | 93 |
| Compound No.46 + Diuron | 100 + 1200 | 1:12 | 100 | 100 | 100 | 100 | 100 |
| | 200 + 1200 | 1:6 | 100 | 100 | 100 | 100 | 100 |

TEST EXAMPLE 14

The test plants in Table 14, which had been treated with the test compositions in Table 15 in the same manner as in Test Example 5, were grown outdoors for 27 days, and the herbicidal activity and phytotoxicity were examined. The results are shown in Table 15.

TABLE 15

| Test compound | Active ingredient dosage (g/ha) | Mixing ratio | Phytotoxicity Cotton | Herbicidal activity | | | | |
|---|---|---|---|---|---|---|---|---|
| | | | | Barn-yard-grass | Johnson-grass | Morning-glories | Slender amaranth | Sickle-pod |
| Fluometuron | 750 | — | none | 70 | 67 | 65 | 85 | 53 |
| | 1500 | — | none | 80 | 80 | 97 | 92 | 68 |
| Compound No. 4 + Fluometuron | 200 + 750 | 1:3.75 | none | 100 | 100 | 100 | 100 | 85 |
| Compound No. 46 + Fluometuron | 50 + 750 | 1:15 | none | 100 | 100 | 100 | 100 | 90 |
| | 100 + 750 | 1:7.5 | none | 100 | 100 | 100 | 100 | 95 |

TEST EXAMPLE 15

The test plants in Table 16, which had been treated with the test composition in Table 16 in the same manner as in Test Example 5, were grown outdoors for 35 days, and the herbicidal activity and phytotoxicity were examined. The results are shown in Table 16.

TABLE 16

| Test compound | Active ingredient dosage (g/ha) | Mixing ratio | Herbicidal activity | | | | |
|---|---|---|---|---|---|---|---|
| | | | Downy brome | Catch-weed bedstraw | Persian speed-well | Field pansy | Common chick-weed |
| Isoproturon | 1000 | — | 55 | 0 | 27 | 0 | 47 |
| | 2000 | — | 62 | 0 | 50 | 0 | 87 |
| Compound No. 4 + Isoproturon | 125 + 1000 | 1:8 | 90 | 100 | 100 | 100 | 97 |

TEST EXAMPLE 16

The test plants in Table 17 were treated with the test compositions in Table 17 and grown in the same manner as in Test Example 6. The herbicidal activity and phytotoxicity were examined. The results are shown in Table 17.

TABLE 17

| Test compound | Active ingredient dosage (g/ha) | Mixing ratio | Phytotoxicity Cotton | Herbicidal activity | | | | |
|---|---|---|---|---|---|---|---|---|
| | | | | Goosegrass | Southern crabgrass | Slender amaranth | Prickly side | Common purslane |
| Trifluralin | 375 | — | none | 17 | 73 | 0 | 17 | 48 |
| Trifluralin | 750 | — | none | 50 | 95 | 27 | 25 | 75 |
| Compound No. 46 + Trifluralin | 100 + 375 | 1:3.75 | none | 100 | 100 | 100 | 100 | 100 |
| Compound No. 55 + trifluralin | 100 + 375 | 1:3.75 | none | 100 | 100 | 100 | 100 | 100 |

The biological data of Compound (I) as a herbicide will be illustrated in the following Reference Test Example wherein the phytotoxicity to crop plants and the herbicidal activity on weeds were determined by visual observation as to the degree of germination as well as the growth inhibition and rated with an index 0, 1, 2, 3, 4, 5, 6, 7, 8, 9 or 10, the numeral "0" indicating no material difference as seen in comparison with the untreated plants and the numeral "10" indicating the complete inhibition or death of the test plants. The compound number in the biological data corresponds to that shown in Table 18.

REFERENCE TEST EXAMPLE 1

Cylindrical plastic pots (diameter, 10 cm; height, 10 cm) were filled with upland field soil, and the seeds of japanese millet, tall morningglory and velvetleaf were sowed therein and covered with soil. A designated amount of the test compound formulated in an emulsifiable concentrate, which was obtained by well mixing of 5 parts of compound (I), 15 parts of "Toxanone P8L" (a commercial surface active agent; Sanyo Kasei K.K.) and 80 parts of cyclomexanon, was diluted with water, and the dilution was sprayed onto the soil surface by means of a small hand sprayer at a spray volume of 1000 liters per hectare. The test plants were grown in a greenhouse for 20 days, and the herbicidal activity was examined. The results are shown in Table 18.

TABLE 18

| Compound No. | Dosage (g/ha) | Herbicidal activity | | |
|---|---|---|---|---|
| | | Japanese millet | Tall morning-glory | Velvet-leaf |
| 1 | 2000 | 9 | 9 | 10 |
| | 500 | 9 | 7 | 9 |
| 2 | 2000 | 9 | 10 | 10 |
| | 500 | 7 | 7 | 7 |
| 3 | 2000 | 10 | 9 | 10 |
| | 500 | 9 | 7 | 8 |
| 4 | 2000 | 10 | 10 | 10 |
| | 500 | 10 | 10 | 10 |
| | 125 | 10 | 10 | 8 |
| 5 | 2000 | 10 | 10 | 10 |
| | 500 | 9 | 10 | 8 |
| | 125 | 8 | 9 | — |
| 6 | 2000 | 10 | 10 | 10 |
| | 500 | 10 | 10 | — |
| 7 | 2000 | 9 | 10 | 10 |
| | 500 | 9 | 8 | — |
| 8 | 2000 | 8 | 9 | — |
| | 500 | 7 | 8 | — |
| 9 | 2000 | 10 | 10 | 10 |
| | 500 | 10 | 10 | — |
| 10 | 2000 | 10 | 10 | 9 |
| | 500 | 10 | 9 | — |
| 11 | 2000 | 10 | 10 | 10 |
| 12 | 2000 | 10 | 9 | 10 |
| 13 | 2000 | 10 | 10 | 9 |
| | 500 | 10 | 10 | 9 |
| 14 | 2000 | 10 | 10 | 10 |
| | 500 | 10 | 10 | — |
| 15 | 2000 | 10 | 10 | 10 |
| | 500 | 9 | 9 | — |
| 16 | 2000 | 10 | 9 | 7 |
| | 500 | 10 | 8 | — |
| 17 | 2000 | 10 | 10 | 10 |
| | 500 | 10 | 10 | 10 |
| 18 | 2000 | 10 | 10 | — |
| | 500 | 10 | 10 | — |
| 19 | 2000 | 10 | 10 | — |
| | 500 | 10 | 7 | — |
| 20 | 2000 | 10 | 10 | 10 |
| | 500 | 10 | 9 | 10 |
| 21 | 2000 | 10 | 9 | — |
| | 500 | 10 | 9 | — |
| 22 | 2000 | 10 | 10 | 10 |
| | 500 | 10 | 9 | 9 |
| | 125 | 9 | 9 | 8 |
| 23 | 2000 | 10 | 10 | 10 |
| | 500 | 10 | 10 | 10 |
| | 125 | 9 | 9 | 8 |
| 24 | 2000 | 10 | 10 | — |
| | 500 | 9 | 9 | — |
| 25 | 2000 | 10 | 10 | 8 |
| | 500 | 10 | 10 | 7 |
| 26 | 2000 | 10 | 10 | 8 |
| | 500 | 10 | 9 | 7 |
| 27 | 2000 | 9 | 10 | 10 |
| | 500 | 9 | — | 10 |
| 28 | 2000 | 9 | 7 | 8 |
| | 500 | 9 | — | 7 |
| 29 | 2000 | 9 | 10 | 9 |
| | 500 | 9 | 10 | 7 |
| 30 | 2000 | 10 | 10 | 10 |
| | 500 | 9 | 8 | 10 |
| 31 | 2000 | 10 | 10 | — |
| 32 | 2000 | 9 | 10 | 7 |
| | 500 | 7 | 8 | — |
| 36 | 2000 | — | 10 | 10 |
| 37 | 2000 | 10 | 10 | 10 |
| | 500 | 10 | 10 | 10 |
| | 125 | 7 | 8 | 7 |
| 38 | 2000 | 9 | 10 | 10 |
| | 500 | 8 | 9 | 10 |
| 39 | 2000 | 10 | 10 | 9 |

TABLE 18-continued

| Compound No. | Dosage (g/ha) | Herbicidal activity | | |
|---|---|---|---|---|
| | | Japanese millet | Tall morning-glory | Velvet-leaf |
| | 500 | 10 | 7 | 7 |
| 40 | 2000 | 10 | 10 | 10 |
| | 500 | 10 | 8 | 7 |
| 41 | 2000 | 10 | 10 | 10 |
| | 500 | 10 | 10 | — |
| 42 | 2000 | 10 | 10 | 10 |
| | 500 | 10 | 10 | 9 |
| 43 | 2000 | 10 | 10 | 10 |
| | 500 | 10 | 10 | 9 |
| 44 | 2000 | 10 | 10 | 10 |
| | 500 | 10 | 10 | 9 |
| 45 | 500 | 10 | 10 | 9 |
| 46 | 500 | 10 | 10 | 10 |
| | 125 | 10 | 10 | 10 |
| 47 | 500 | 10 | 10 | 10 |
| | 125 | 10 | 10 | 10 |
| 48 | 500 | 9 | 9 | 9 |
| | 125 | 8 | 8 | 8 |
| 49 | 500 | 9 | 10 | 9 |
| 50 | 500 | 10 | 10 | 8 |
| | 125 | 9 | 7 | 7 |
| 51 | 2000 | 7 | 9 | 9 |
| 52 | 500 | 10 | 10 | 10 |
| 53 | 500 | 10 | 10 | 10 |
| | 125 | 9 | 10 | 7 |
| 54 | 2000 | 10 | 10 | 9 |
| 55 | 500 | 10 | 10 | 10 |
| | 125 | 10 | 10 | 10 |
| 56 | 500 | 10 | 10 | 10 |
| | 125 | 9 | 9 | 7 |
| 57 | 500 | 10 | 10 | 10 |
| | 125 | 9 | 10 | 10 |
| 58 | 2000 | 10 | 10 | 7 |
| | 500 | 10 | 10 | 7 |
| 59 | 2000 | 10 | 10 | 10 |
| | 500 | 10 | 10 | 10 |
| 60 | 2000 | 10 | 10 | 10 |
| | 500 | 10 | 10 | 10 |
| 61 | 2000 | 10 | 10 | 10 |
| | 500 | 10 | 10 | 10 |
| 62 | 2000 | 7 | 7 | 7 |
| 64 | 2000 | 9 | 10 | 7 |
| 65 | 500 | 9 | 10 | 10 |
| 66 | 500 | 7 | 8 | 7 |
| 67 | 500 | 10 | 10 | 10 |
| | 125 | 9 | 10 | 9 |
| 68 | 500 | 9 | 9 | 8 |
| 69 | 500 | 9 | 9 | 8 |
| 70 | 500 | 9 | 9 | 10 |
| | 125 | 8 | 8 | 8 |

What is claimed is:

1. A herbicidal composition comprising as active ingredients a herbicidally effective amount of:
(a) an iminothiazoline compound of the formula:

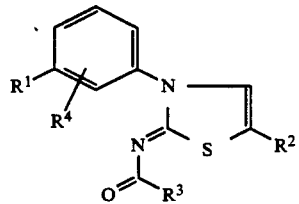

wherein $R^1$ is halogen, halo($C_1$-$C_2$)alkyl, halo($C_1$-$C_2$)alkoxy or halo($C_1$-$C_2$)alkylthio; $R_2$ is $C_1$-$C_2$ alkyl, chlorine, bromine or iodine; $R^3$ is $C_1$-$C_6$ alkyl, $C_3$-$C_6$ cycloalkyl, $C_3$-$C_6$ cycloalkoxy or $C_1$-$C_6$ alkoxy, all of which are optionally substituted with at least one substituent selected from halogen, $C_1$-$C_2$ alkyl and $C_1$-$C_2$ alkoxy; $R^4$ is hydrogen or halogen; and (b) at least one of herbicidal triazine compounds, herbicidal uracil compounds, herbicidal urea compounds, herbicidal dinitro aniline compounds, norflurazon, dimethazone, imazaquin and imazethapyr.

2. A composition according to claim 1, wherein said ingredient (b) is selected from the herbicidal triazine compounds.

3. A composition according to claim 2, wherein said ingredient (b) is at least one of atrazine, cyanazine, prometryn and metribuzin.

4. A composition according to claim 1, wherein said ingredient (b) is selected from the herbicidal uracil compounds.

5. A composition according to claim 4, wherein said ingredient (b) is at least one of isoprocil, bromacil and lenacil.

6. A composition according to claim 1, wherein said ingredient (b) is selected from the urea compounds.

7. A composition according to claim 6, wherein said ingredient (b) is at least one of fenuron, monuron, monolinuron, buturon, diuron, linuron, metoxuron, chlorotoluron, isoproturon and fluometuron.

8. A composition according to claim, 1, wherein said ingredient (b) is selected form the herbicidal dinitro aniline compounds.

9. A composition according to claim 8, wherein said ingredient (b) is at least one of trifluralin, benefin, pendimethalin, oryzalin, ethalfluralin and prodiamine.

10. A composition according to claim 1, wherein said ingredient (b) is norflurazon.

11. A composition according to claim 1, wherein said ingredient (b) is dimethazone.

12. A composition according to claim 1, wherein said ingredient (b) is at least one of imazaquin and imazethapyr.

13. A composition according to claim 1, wherein $R^1$ is halo($C_1$-$C_2$)alkyl, $R^2$ is $C_1$-$C_2$ alkyl, $R^3$ is $C_1$-$C_6$ alkoxy, $C_1$-$C_6$ alkyl or halo($C_1$-$C_6$)alkyl, $R^4$ is hydrogen or fluorine at the para position.

14. A method for controlling undesired weeds, which comprises applying the composition according to claim 1 to the area where undesired weeds grow or will grow.

15. A method for controlling undesired weeds, applying the composition according to claim 1 to the area where undesired weeds grow or will grow, which comprises wherein the area is a field of cotton, soybean or rice plant.

16. A composition according to claim 1, wherein $R^1$ is selected from the group consisting of trifluoromethyl, trifluoromethoxy, fluoro, bromo, and chloro; $R^2$ is selected from the group consisting of bromo, iodo, methyl and ethyl; $R^3$ is selected from the group consisting of ethoxy, phenoxy, n-propoxy, 2-chloromethyl, i-propyl, n-propyl, trifluoromethyl, pentafluoroethyl, heptafluoroethyl, 2-methylcyclopropyl, difluoromethyl, i-propoxy, and cyclopropyl; and $R^4$ is selected from the group consisting of hydrogen, 4-fluoro, 6-fluoro and 4-chloro.

17. A composition according to claim 1, wherein $R^1$ is trifluoromethyl; $R^2$ is methyl; $R^3$ is $C_1$-$C_6$ alkyl substituted with fluorine; and $R^4$ is hydrogen.

18. A composition according to claim 17, wherein $R^3$ is methyl substituted with fluorine.

19. A composition according to claim 17, wherein $R^3$ is difluoromethyl or trifluoromethyl.

20. A composition according to claim 1, wherein $R^1$ is trifluoromethyl, $R^2$ is methyl, $R^3$ is difluoromethyl and $R^4$ is hydrogen.

* * * * *